(12) United States Patent  (10) Patent No.: US 8,232,506 B2
Jussel  (45) Date of Patent: Jul. 31, 2012

(54) DENTAL FIRING FURNACE

(75) Inventor: Rudolf Jussel, Feldkirch-Tosters (AT)

(73) Assignee: Ivoclar Vivadent AG, Schaan (LI)

( * ) Notice: Subject to any disclaimer, the term of this patent is extended or adjusted under 35 U.S.C. 154(b) by 1045 days.

(21) Appl. No.: 12/080,065

(22) Filed: Mar. 30, 2008

(65) Prior Publication Data

US 2008/0237211 A1 Oct. 2, 2008

Related U.S. Application Data

(60) Provisional application No. 60/931,580, filed on May 24, 2007.

(30) Foreign Application Priority Data

Mar. 30, 2007 (DE) .......................... 10 2007 015 435

(51) Int. Cl.
*F27B 5/14* (2006.01)
*A61C 19/00* (2006.01)
(52) U.S. Cl. ............ 219/390; 219/393; 433/25; 433/32; 433/218; 433/219; 433/223
(58) Field of Classification Search .................. 219/390, 219/393; 433/25, 32, 218, 219, 223, 227; 75/57, 60
See application file for complete search history.

(56) References Cited

U.S. PATENT DOCUMENTS

| | | | | |
|---|---|---|---|---|
| 4,272,670 A * | 6/1981 | Docx | ............................ | 219/390 |
| 4,828,490 A | 5/1989 | Indig | | |
| 6,180,922 B1 * | 1/2001 | Rohner et al. | ................ | 219/390 |
| 6,303,059 B1 | 10/2001 | Foser et al. | | |
| 6,384,382 B2 * | 5/2002 | Rohner et al. | ................ | 219/413 |
| 6,935,407 B2 | 8/2005 | Shikata | | |
| 2008/0096148 A1 | 4/2008 | Jussel | | |

FOREIGN PATENT DOCUMENTS

| | | |
|---|---|---|
| CA | 2034893 A1 | 7/1991 |
| DE | 3146391 A1 | 5/1983 |
| DE | 33 15 835 A1 | 11/1984 |
| DE | 3315835 C2 | 11/1984 |
| DE | 3719536 C2 | 12/1987 |
| DE | 196 06 493 C1 | 9/1997 |
| DE | 19606493 C1 | 9/1997 |
| DE | 19844136 A1 | 4/2000 |
| DE | 10313406 A1 | 10/2004 |
| DE | 10327892 B3 | 12/2004 |
| DE | 202006004578 U1 | 7/2006 |
| EP | 0438802 A1 | 7/1991 |
| EP | 1127555 A1 | 8/2001 |
| EP | 1915972 A1 | 4/2008 |
| WO | 03/011168 | 2/2003 |

* cited by examiner

*Primary Examiner* — Shawntina Fuqua
(74) *Attorney, Agent, or Firm* — Hodgson Russ LLP

(57) ABSTRACT

The present invention relates to a dental firing furnace having a firing space and at least one carrier for dental material, in particular a muffle, which can be loaded into the firing space, and, in particular, a pressing device for pressing a ceramic blank inserted in the muffle, at least one physical variable of the firing space and/or of the carrier and/or of the muffle and/or of the ceramic blank being detected. A processing program of the dental furnace (10) that can be set is based on the detected physical variable.

11 Claims, 2 Drawing Sheets

DENTAL FIRING FURNACE

CROSS-REFERENCE TO RELATED APPLICATIONS

This application claims foreign priority benefits under 35 U.S.C. §119(a)-(d) from German patent application ser. no. P 10 2007 015 435.8 filed Mar. 30, 2007. In addition, this application claims the benefit under 35 U.S.C. §119(e) of U.S. provisional patent application Ser. No. 60/931,580 filed May 24, 2007.

TECHNICAL FIELD

The invention relates to a dental firing furnace, and more particularly to a dental firing furnace provided with a firing space and a carrier for dental material which can be loaded into the firing space, and a pressing device for pressing a ceramic blank inserted in the carrier, and including a processing program which can be set on the basis of a detected physical variable.

BACKGROUND OF THE INVENTION

DE 33 15 835 C2 discloses a vacuum pressure casting device that uses a crucible with melt material. Via a site-mounted thermocouple, it is intended to detect temperature changes that are caused by the melt material, even if only small quantities of melt material are introduced.

It is true that this solution as presented aims at implementing a quick adaptation of the firing furnace temperature via a main controller and an auxiliary controller, protection against overtemperature also being built in. However, this solution is not suitable in principle if, apart from the quantity of material provided for melting, the temperature thereof is also different.

Furthermore, it is known per se from DE 196 06 493 C1 also to measure the temperature of the firing material in a dental firing furnace in the immediate vicinity of the firing material. It is provided in this solution to move the firing material in order to balance the desired temperature with the actual temperature along a temperature gradient. However, this brings about a corresponding vibration of the firing material that is not desired in some cases. In particular, this solution is also not suitable if use is made of a press furnace since the effect of the press ram that is built into the furnace hood is to fix the site at which the muffle must be located as carrier for the firing material.

Furthermore, it has already been proposed per se to evaluate the measured temperatures via a very complicated control device, and to adapt the firing temperature to the requirements. For example, there is a difference between the sintering temperatures for different ceramic materials from which dental restoration parts are produced, and the sinter firings must proceed with a temperature profile other than, for example, a glaze firing. It has also become known to display the firing curve graphically in order to provide the dental technician with better information.

Finally, it has also become known to use preheating furnaces that preheat the ceramic blanks to the temperature desired in each case, and this can differ depending on the ceramic. The prepared muffle can thus be set to the preheating temperature such that the temperature gradients in the actual press furnace are reduced during pressing. However, it is possible thereby not only for the muffle sizes themselves to differ, but different ceramics can also be used such that there is respectively a need for a very complicated adaptation in order to set the optimum temperature profile for the sinter firing. These different requirements can be met only inadequately with the furnaces known to date.

OBJECTS AND SUMMARY OF THE INVENTION

It is therefore the object of the invention to create a dental firing furnace provided with a firing space and a carrier for dental material which can be loaded into the firing space, and a pressing device for pressing a ceramic blank inserted in the carrier and including a processing program can be set on the basis of the detected physical variable, which is also particularly well suited precisely for use in conjunction with preheating furnaces.

It is provided according to the invention to detect the physical size at least of the muffle or the ceramic blank that can be inserted there, or else detect that of the some other carrier, and to set a processing program of the dental firing furnace on the basis thereof, that is to say to undertake an optimization automatically, as it were. It goes without saying that the remaining furnace parameters such as, for example, the size of the firing space, must be taken into account when selecting the processing program, and that the dental firing furnace is otherwise calibrated in a fashion known per se with regard to temperature measurement.

It is particularly advantageous when the size of the carrier, which also to this extent includes its mass, is taken into account when selecting the processing program. It is thereby possible to prevent the ceramic blank and the muffle from being heated too rapidly, something which can lead to stress cracks, but also to prevent heating too slowly, which unnecessarily lengthens the cycle time.

For example, after the introduction of the muffle fitted with the ceramic blank a prescribed heating power is fed from the preheating furnace into the dental firing furnace for a defined time period. The temperature increase implemented thereby in the muffle is detected. In the event of a comparatively quick heating of the muffle, it can consequently be established that a muffle is present which has a correspondingly lower thermal capacity, that is to say a smaller muffle size, whereas in the event of a long heating time or a relatively small temperature increase it can be assumed that a muffle is present which has a relatively large thermal capacity.

Consequently, it is then possible on the basis of this knowledge to optimize the heating power for the actual sintering operation or pressing operation to be optimized such that in the case of a relatively large muffle more heating power is thus automatically introduced in order to provide the same temperature increase per time as in the case of a relatively small muffle. The dental firing furnace according to the invention is to this extent suitable for automatic detection or muffle detection even in the case of very different muffle sizes, it being possible, for example, even for a muffle size of factor 3 also to be covered straightaway.

The solution according to the invention also permits compensation of the cooling that goes ahead during transfer from the preheating firing furnace into the dental firing furnace. The time in which the cooling occurs and, correspondingly, the extent of the cooling, depend, on the one hand, on the muffle size, and on the other hand on the distance between the preheating furnace and dental firing furnace and, finally, also on the rate at which the dental technician is working. According to the invention, it is particularly favorable when an appropriately adapted desired temperature profile is provided that manages with a shorter preheating time such that the cycle time is reduced overall.

It is particularly advantageous according to the invention when use is made of a thermal sensor that specifically detects the temperature of the surface of the carrier, in particular, therefore, the muffle, preferably without touching the latter. Such a detection permits the muffle temperature to be determined independently of the wall temperature of the dental firing furnace.

The sensor according to the invention is not limited to the use of a thermal sensor. Rather, it is also advantageously possible to use a size sensor or a weight sensor that detects the size and/or weight of the carrier, that is to say of the muffle, if appropriate.

It is provided in an advantageous refinement also to incorporate the introduced underpressure and/or the pressing device in the monitoring. For example, it is possible to detect the path covered by the pressing device, and/or a pressure change, in order to monitor the melting of the ceramic blank and the progress of pressing.

The sensor can be used to detect not only the temperature that, in conjunction with an evaluation device, serves for selecting the processing program, but also the temperature profile, or else, for example, also a temperature gradient, that is to say the temperature difference between two types in the interior of the dental firing furnace, but also a temperature change in the firing space after the loading of the muffle.

The invention is also not limited to the implementation of a dental firing furnace having a pressing device, that is to say so-called press furnace. Rather, it is also possible to fit an unpressurized dental firing furnace or a dental casting furnace in a way according to the invention.

In an advantageous refinement of the invention, there is provided a position measuring system, for example pulse detection of a stepping motor or a potentiometer, via which the distance between an initial position of the pressing device and the ceramic blank inserted in the muffle is determined, and, with the muffle loaded into the firing space, is determined for the purpose of further increasing the firing space temperature that the quantity of heat additionally introduced conducts within specific time period.

The position measuring system can be implemented by the detection of a path length covered by the stepping motor for the pressing device, and the pressure of the pressing device can also be determined by measuring the drive current of the motor.

It is also possible in the case of this solution to detect how long the ceramic blank is—or, if appropriate, how long two ceramic blanks inserted one in—are. It is also possible to this extent to implement an automatic adaptation of the processing program in a way according to the invention.

It is further provided that the processing program of the dental firing furnace has a preheating section that can be set via the detected physical variable. In the case of this solution, the actual sintering operation or pressing operation can then be implemented in the optimized way, while during the preheating section the differences between the individual muffles or other carriers converge.

Furthermore, it may be favorable to control the temperature of the dental firing furnace during preheating to a desired temperature of the muffle at the end of the preheating section or, for example, by a slight temperature difference below or above this temperature. This provides the optimized, always similar initial conditions for the actual firing cycle.

On the other hand, the difference between various muffles can automatically always be detected in the best way whenever the temperature difference is substantial, since the reaction time then turns out to be different depending on muffle size.

According to the invention, heat is particularly advantageous, furthermore, when the specific thermal capacity of the relevant parts of the firing space hood is incorporated into the calculation. In this case, in particular, account is to be taken of the part of the firing space hood that runs between the heating device and the muffle, that is to say a quartz glass cover, by way of example.

In a further advantageous refinement, it is provided that in the dental firing furnace the detected physical variable influences the processing program directly in particular, automatically, in particular the size of a muffle being detected indirectly or directly.

In a further advantageous refinement, it is provided that the temperature difference between the firing space and the carrier is detected, and the thermal capacity of the carrier is detected on the basis of the rate of change in the temperature of the carrier.

In a further advantageous refinement, it is provided that a sensor in the dental firing furnace detects the physical variable and relays it to a control device that controls the processing program of the dental firing furnace automatically as a function of the detected variable.

In a further advantageous refinement, it is provided that the muffle is heated in a preheating furnace, and is inserted into the dental firing furnace at a prescribed temperature.

In a further advantageous refinement, it is provided that before the insertion of the preheated muffle the dental firing furnace is kept at a readiness temperature, and after the insertion of the muffle the change in the temperature of the firing space and, in particular, also the rate of change are detected.

In a further advantageous refinement, it is provided that the muffle is inserted into the firing space at a temperature that diverges from the readiness temperature of the dental firing furnace, in particular being greater than said temperature.

In a further advantageous refinement, it is provided that the temperature difference between the firing space and the muffle preheated in a preheating furnace is detected, and the thermal capacity of the muffle is detected on the basis of the rate of change of the temperature in the firing space.

In a further advantageous refinement, it is provided that the relative temperature between the firing space and the preheated muffle is measured, and the rate of change in the firing space temperature in relation to said temperature difference is used as physical variable.

In a further advantageous refinement, it is provided that at least two different muffle sizes can be used, and the processing program is set automatically to that muffle size which is closest to the measured muffle size.

In a further advantageous refinement, it is provided that a pressure sensor is provided via which the resilience of the ceramic blank loaded into the muffle and subjected to pressure by the pressing device is detected, and the setting of the processing program is undertaken as a function thereof.

In a further advantageous refinement, it is provided that a position measuring system, for example the pulse detection of a stepping motor or a potentiometer, is provided via which the compressed ceramic blank inserted in the muffle between an initial position of the pressing device and the current position of the press ram is detected.

In a further advantageous refinement, it is provided that the firing space temperature of the dental firing furnace is detected, on the one hand, before the insertion of the muffle and, on the other hand, after the insertion of the muffle, in particular at a prescribed point in time after the insertion of the muffle, and the size of the muffle is determined from the temperature change and/or the temperature change gradient.

In a further advantageous refinement, it is provided that in the muffle loaded into the firing space in order to further increase the firing space temperature the quantity of heat generated by the dental firing furnace and additionally introduced is detected within a specific time period.

Further advantages, details and features emerge from the following description of two exemplary embodiments with the aid of the drawing, in which:

DETAILED DESCRIPTION

Figure 1:
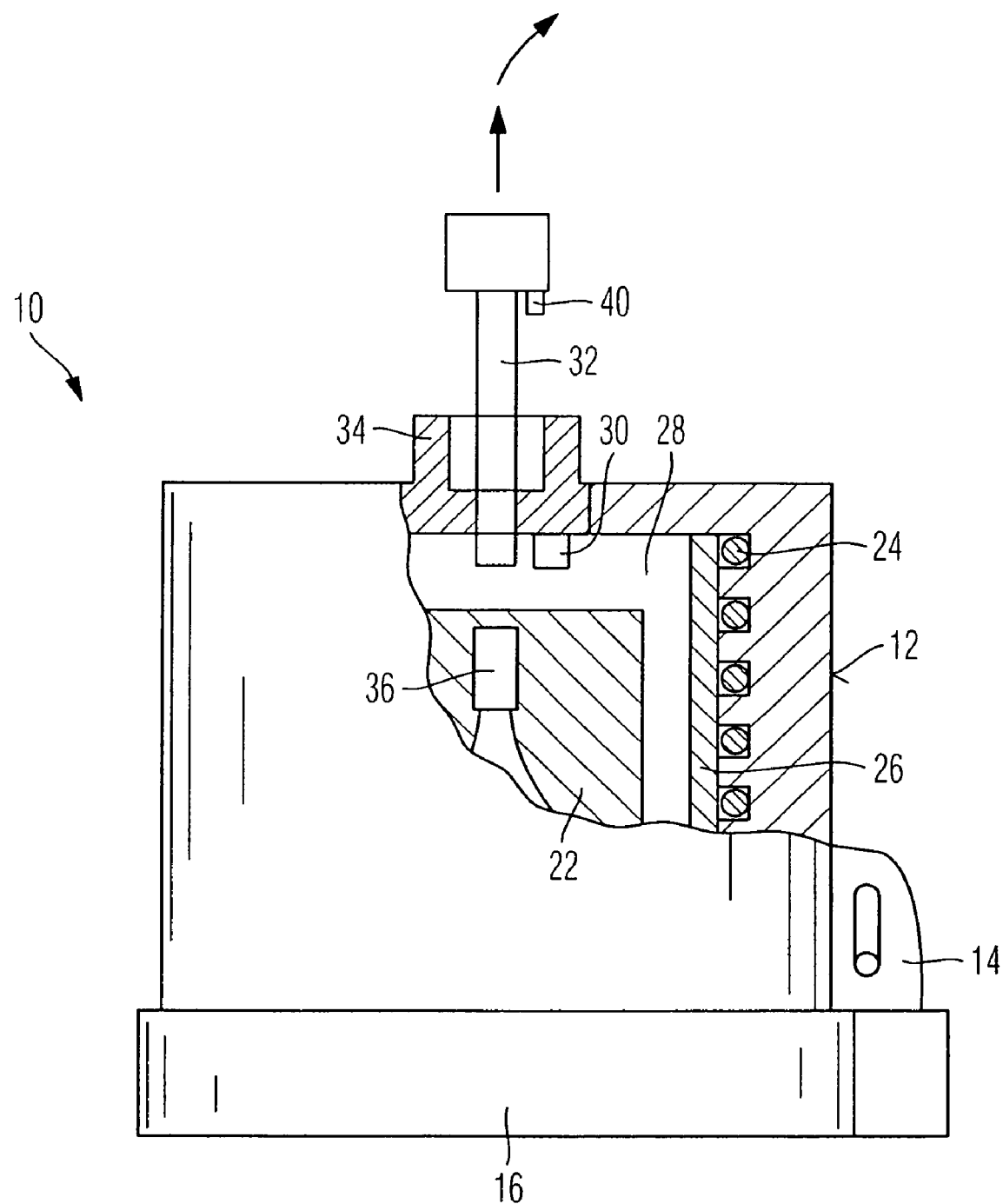
FIG. 1 is a schematic of a press furnace as an embodiment of a dental firing furnace according to the invention, in a partially cutaway illustration.

The dental firing furnace 10 illustrated in FIG. 1 has a furnace hood 12 that can be removed from a baseplate 16 in a way known per se via a joint 14. A lifting/swiveling movement such as is known per se is preferably possible. The baseplate 16 holds a carrier 20, a muffle 22 being used here as carrier.

In its side wall, the furnace hood 12 holds a heater 24 that covers a quartz tube 26. The heater 24 serves for heating a firing space 28 in which the muffle 22 is loaded.

According to the invention, a temperature sensor 30 (visible merely schematically) is provided which can be combined with a pressure sensor (not illustrated). In this embodiment, the pressure sensor detects the pressure applied to the ceramic blank 36 by a pressing device 32 via a press ram 34. A position sensor 40 that detects how the press ram 34 of the pressing device 32 moves downward is additionally provided in this embodiment.

In order to operate the dental firing furnace 10 according to the invention, the dental firing furnace 10 is firstly heated to a specific temperature, for example to 800° C. A muffle 22 with ceramic blank 36 already loaded is preheated, for example to 700° C., in a preheating furnace (not illustrated here).

To start the actual pressing operation, the muffle 22 is removed from the preheating furnace and loaded into the dental firing furnace 10 after the opening of the furnace hood 12, whereupon the furnace hood 12 is rapidly reclosed. The muffle loses temperature somewhat owing to the transportation, so that it has, for example, a temperature of 660° at its surface, which is detected via the temperature sensor 30.

The dental firing furnace 10 is now firstly kept for an added period of time of, for example, 60 seconds in the region of the heating device 12, that is to say on the quartz tube 26, at a temperature of 700° C. This temperature can also likewise drop slightly (temperature difference approximately 40° C.) owing to the influence of the relatively cool muffle 22.

A measurement is then taken to find out which temperature has arisen at the surface of the muffle 22 after 60 seconds. Depending on the magnitude of the temperature, a conclusion is then drawn as to the mass selected on the basis thereof. According to the invention, use is made here advantageously of the fact that large muffles are typically used in relatively large dental restorations which, if appropriate, also require the use of two or three ceramic blanks that are introduced into the muffle channel one after another, that is to say one above another.

Figure 2:
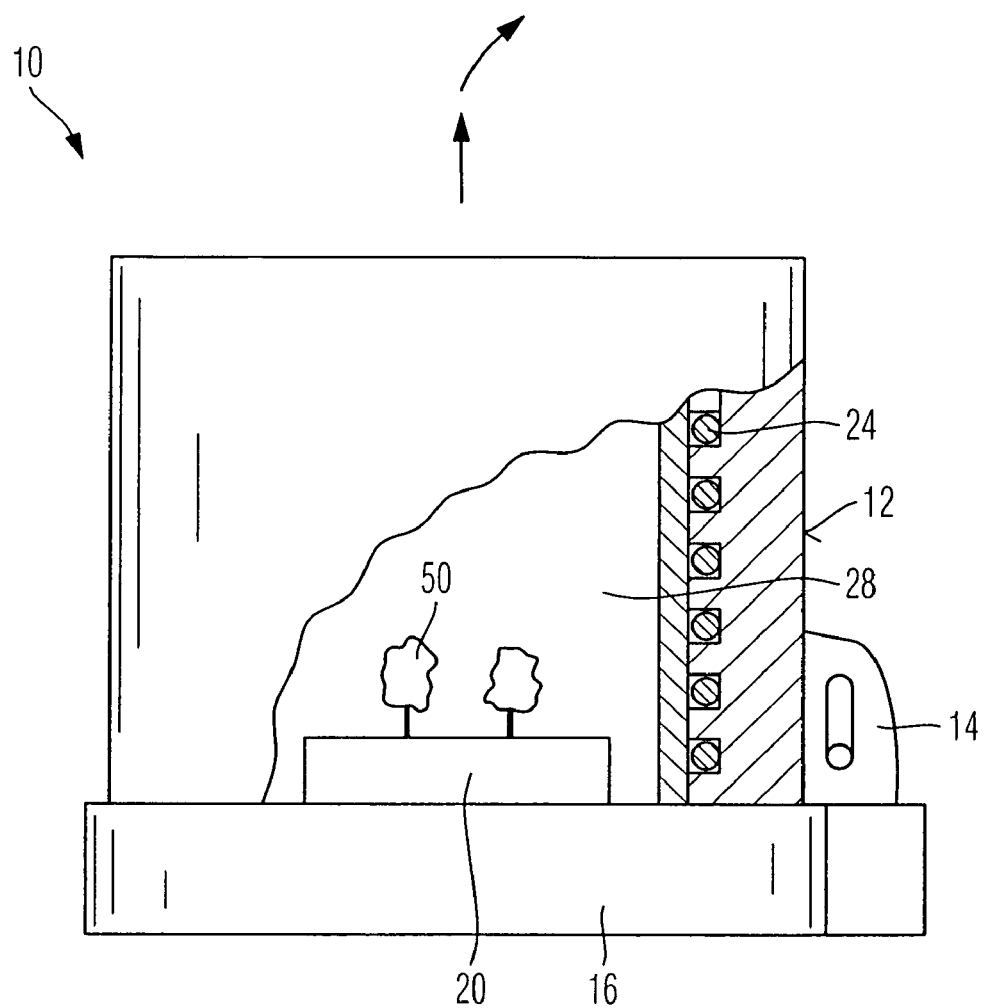
FIG. 2 shows an unpressurized dental firing furnace in a further embodiment of a dental firing furnace according to the invention, likewise illustrated in a partially cutaway fashion.

A similar operating method according to the invention can also be implemented in the case of a dental firing furnace 10 in accordance with FIG. 2 that has no pressing device. Identical reference symbols refer here to identical parts. In this embodiment, the dental restoration part 50 is held in a known way on a carrier 20. Together with the carrier 20, its mass is decisive here for the reaction or step response to the loading, and so the suitable firing profile for the optimized sintering of the dental restoration parts 50 can also be provided here.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A dental firing furnace in combination with a muffle which has received a ceramic blank, the furnace having
a firing space (28), which can receive the muffle,
a pressing device (32) for pressing a ceramic blank (36) inserted into the muffle (22) to form a dental restoration part when properly fired,
sensor means for monitoring over time the temperature difference between the firing space (28) and the muffle (22), and
a control device, which automatically controls a processing program of the dental firing furnace (10) as a function of the monitored temperature difference over time to cause the furnace to properly fire a dental restoration part formed from the ceramic blank, the rate of change of the firing space temperature in relation to said temperature difference serving as a physical variable for setting a processing program of the dental furnace and automatically influencing the same, wherein the detected temperature difference over time provides for an indirect detection of the size of the muffle (22).

2. The dental firing furnace as claimed in claim 1 wherein the thermal capacity of the carrier (20) may be detected on the basis of the rate of change in the temperature of the carrier (20).

3. The dental firing furnace as claimed in claim 1 wherein the thermal capacity of the muffle (22) may be detected on the basis of the rate of change in the temperature within the firing space (28).

4. The dental firing furnace as claimed in claim 1, wherein the dental firing furnace is further in combination with a preheating furnace, the muffle (22) inserted into the dental firing furnace having been heated in a preheating furnace at a prescribed temperature.

5. The dental firing furnace as claimed in claim 4, wherein before the insertion of the preheated muffle (22), the dental firing furnace (10) may be kept at a readiness temperature, and after the insertion of the muffle (22) the change in the temperature of the firing space (28) and also the rate of change may be detected.

6. The dental firing furnace as claimed in claim 1 wherein the muffle (22) prior to its insertion into the firing space (28) has a temperature that diverges from the readiness temperature of the dental firing furnace (10), in particular is greater than said temperature.

7. The dental firing furnace as claimed in claim 1, wherein at least two different muffle sizes may be inserted, and the processing program may be automatically set to that muffle size which is closest to the measured muffle size.

8. The dental firing furnace as claimed in claim 1, wherein a pressure sensor is provided via which the resilience of the ceramic blank (36) loaded into the muffle (22) and subjected to pressure by the pressing device (32) may be detected, and the setting of the processing program is carried out as a function thereof.

9. The dental firing furnace as claimed in claim 1, wherein a position measuring system is provided via which the non-pressed ceramic blank (36) inserted into the muffle (22) between an initial position of the pressing device (22) and the current position of the press ram (34) may be detected.

10. The dental firing furnace as claimed in claim 1, wherein the firing space temperature of the dental firing furnace (10) may be detected, on the one hand, before the insertion of the muffle (22) and, on the other hand, after the insertion of the muffle (22), in particular at a prescribed point in time after the insertion of the muffle (22), and the size of the muffle (22) may be determined from the temperature change and/or the temperature change gradient.

11. The dental furnace as claimed in claim 1, wherein in the muffle (22) loaded into the firing space (28) in order to further increase the firing space temperature, the quantity of heat generated by the dental firing furnace and additionally introduced may be detected within a specific time period.

\* \* \* \* \*